US005698184A

United States Patent [19]

Pickart

[11] Patent Number: 5,698,184
[45] Date of Patent: Dec. 16, 1997

[54] COMPOSITIONS AND METHODS FOR SKIN TANNING AND PROTECTION

[75] Inventor: Loren R. Pickart, Bellevue, Wash.

[73] Assignee: Skin Biology, Inc., Bellevue, Wash.

[21] Appl. No.: 702,225

[22] Filed: Aug. 23, 1996

[51] Int. Cl.⁶ .............................. A61K 7/42; A61K 38/16
[52] U.S. Cl. .................................. 424/59; 514/6
[58] Field of Search .................... 424/59; 514/2, 514/492, 493, 500, 499, 917, 6

[56] References Cited

U.S. PATENT DOCUMENTS

| 4,123,511 | 10/1978 | Heintze . | |
|---|---|---|---|
| 4,156,737 | 5/1979 | Bertelli . | |
| 4,504,644 | 3/1985 | Lang et al. | 527/201 |
| 4,760,051 | 7/1988 | Pickart . | |
| 4,921,942 | 5/1990 | Bernhardt et al. | 424/59 |
| 5,023,237 | 6/1991 | Pickart . | |
| 5,118,665 | 6/1992 | Pickart . | |
| 5,120,831 | 6/1992 | Pickart . | |
| 5,348,943 | 9/1994 | Pickart . | |
| 5,382,431 | 1/1995 | Pickart | 424/401 |
| 5,462,963 | 10/1995 | Bush et al. | 514/248 |
| 5,582,817 | 12/1996 | Otsu et al. | 424/59 |

FOREIGN PATENT DOCUMENTS 450398  10/1991  European Pat. Off. .

*Primary Examiner*—Raymond Henley, III
*Attorney, Agent, or Firm*—Townsend and Townsend and Crew

[57] ABSTRACT

Compositions of peptones and ionic metals stimulate melanogenic activity in the skin while simultaneously protecting the skin from damage due to ultraviolet light. The compositions are useful in skin tanning and increasing pigmentation, and in healing skin damaged from exposure to ultraviolet light.

11 Claims, No Drawings

COMPOSITIONS AND METHODS FOR SKIN TANNING AND PROTECTION

BACKGROUND OF THE INVENTION

Suntanning is of social significance in many parts of the world. The aesthetic properties of a suntan are due to an increased melanin pigmentation (brown to black) combined with a redness due to skin erythema. For cosmetic purposes, one approach to increase skin pigmentation is by exposure to sunlight or ultraviolet (UV) sunlamps. The tanned skin is almost universally regarded as a positive aesthetic attribution, particularly among a high proportion of light skinned (Caucasian) individuals. Unfortunately suntanning is often followed by the peeling and loss of the tanned skin, especially in light skinned individuals, which leads to more suntanning and a pattern of excessive overexposure to sunlight, with certain attendant dangers such as skin cancer.

The color of human skin is primarily due to the redness of blood cells combined with the presence of melanin pigment within the skin, which pigment is usually in the form of discrete granules called melanosomes. The melanosomes are generated in the viable layer of epidermis by pigment cells (melanocytes). The skin color is genetically controlled and people of different races exhibit characteristic features of pigmentation both in their intensity and chromatic tone. The depth of color in human skin is a function of the quantity of the melanin pigment present, its chemical characteristics and distribution. The presence of melanin in the skin provides a marked photoprotective role, i.e., it acts as an oxygen radical scavenger and blocks ultraviolet radiation.

Some effects of exposure to sunlight are beneficial. The tanning response enables the natural defenses against ultraviolet radiation to be strengthened by increasing the proportion of melanin in the epidermis. Also, vitamin D is synthesized in skin exposed to UV radiation. A deficiency of this vitamin in the body can cause rickets. A lack of adequate sunlight can produce depression and despondency, known clinically as seasonal affect disorder (SAD). Animal studies suggest that increased exposure to sunlight is a stimulant to sexual drive and may serve to time the mating cycles in regions in the higher latitudes. In humans, exposure to sunlight over the body often results in a sense of well-being and improved self-esteem which, in turn, may affect sexual self-esteem. Overall, ultraviolet-induced melanogenesis may be one part of a eukaryotic SOS response to damaging ultraviolet irradiation that has evolved over time to provide a protective tan in skin at risk of further injury from sun exposure.

Other conditions exist where increased tanning or pigmentation is desirable. In some persons, a condition called "vitiligo" occurs whereby patches of lightly pigmented skin exist surrounded by darker pigmented skin. Vitiligo predominately occurs on the head, neck and genitals. The condition can produce adverse physiological effects and often the de-pigmented skin is surgically excised. This condition is most troubling in darker pigmented individuals but even persons from lightly pigmented groups have been known to have the de-pigmented skin surgically removed.

The three methods for tanning skin are exposure to sunlight or artificial ultraviolet rays produced by sunlamps, the use of agents that artificially dye the skin, and the use of agents that increase the natural levels of melanin in the skin.

Increasing skin pigmentation by sunlight or ultraviolet rays is effective but damages the skin. Contrary to popular belief it is not necessary to engage in sunbathing to suffer skin damage. It has been estimated that over 70% percent of the damage the sun inflicts on the average person's skin over lifetime is the result of simply being outdoors or even sitting by a window.

One of the long term hazards of excessive ultraviolet radiation is malignant changes in the skin surface. Numerous epidemiologic studies demonstrate a strong relationship between sunlight exposure and human skin cancer. Another hazard is premature aging of the skin. This condition is characterized by sagging, wrinkling and yellowing of the skin, along with other physical changes such as crackling, telangiectasis (spider vessels), solar keratoses (growths), ecchymoses or lack of elasticity. And, sunbathing often produces skin burns and consequent skin peeling that removes the desired tanning action. Agents are needed that induce or accelerate the tanning of skin but at the same time provide a protective and healing milieu.

Presently available agents that act by staining the skin provide an artificial tan without exposure to the sun but suffer from several disadvantages. It is difficult to match the natural blend of reddish-brown produced by natural tanning, and different shadings on the skin frequently result due to uneven application on the skin. Further, colored areas are removed non-uniformly during cleaning of the skin. A tan produced by staining last only about 5 days, in contrast to the 10 to 14 week duration of a natural suntan. Additionally, the dye which is employed as the staining agent does not protect the skin against harmful ultraviolet radiation.

One example of an artificial tanning agent which has been widely commercialized is dihydroxyacetone. Dihydroxyacetone preparations may contain up to 50% alcohol, and such alcoholic preparations tend to dry the skin. Another skin staining agent is cuprous chloride used with benzyl alcohol or 2,3-dihydroxy-benzoic acid (U.S. Pat. No. 4,145,413 to Usdin et al.). The oxidation of hydroxylated indoles such as dopamine with sodium iodate is described in U.S. Pat. No. 4,776,857 to Carroll et al. in methods to stain the skin. Derivatives of 3-(3,4-dihydroxy)phenylalanine are described in U.S. Pat. No. 4,508,706 to Herlihy. A number of compositions for enhancing coloration of the skin due to exposure to the sun are described in U.S. Pat. No. 4,021,538, to Pawelek et al., including the salts of aliphatic esters of DOPA or alpha-methyl DOPA. U.S. Pat. Nos. 4,390,341 and 4,453,941 to Jacobs describes compositions of tyrosine and beta-alanine and 0.1M copper chloride as an oxidant for producing pigmentation in human hair and skin to provide variations of the natural colors.

To obtain more rapid coloration the art has turned to the use of metallic salts such as copper or ferrous sulfates and indole, a melanin precursor. The metals serve to catalyze the oxidation of the indole and form melanin or melanin-like compounds. Unfortunately, these salts cause the formation of melanin and skin color only in the outermost surface of the skin such that the resulting color is easily removed by ordinary washings. In addition, the color is often gray rather than tan, contributing to an unpleasant yellow hue of the skin.

U.S. Pat. No. 4,609,544 discloses tanning by applying a composition comprising a melanin-like dye, a peroxidase enzyme and hydrogen peroxide in a cosmetic base suitable for topical application to the skin. U.S. Pat. No. 4,515,773 discloses a skin tanning composition containing a melanin precursor and a tyrosinase enzyme in a cosmetic base. Thus, these compositions require the use of enzymes and oxidative agents in combination with the melanin precursors, and appear to deposit the melanin-like materials on the exterior of the skin. As the melanin molecule is incapable of penetrating the skin, only superficial external tanning results, which is readily removed by rinsing with water or rubbing with a towel. At present there is no commercially available skin staining product that will mimic a natural skin tan with respect to its durability, aesthetics of color and photoprotection.

Methods that increase melanogenesis and thus skin melanin have been developed but they typically do not increase the reddish color of skin that is part of the natural tanning process. U.S. Pat. No. 5,476,651 to Meybeck et al. describes the use of a natural product, an extract of tubers of Cyperus to promote skin pigmentation. Small DNA fragments, particularly thymine dinucleotides (pTpT), selected to mimic sequences excised during the repair of UV-induced DNA photoproducts, have been used to induce in a pigment tanning response in guinea pig skin. Eller et al., *Proc. Natl. Acad. Sci. USA* 93:1087–92 (1996). Topical application of the diacylglycerol (DAG), 1-oleoyl-2-acetyl-sn-glycerol, to the skin for 5 days markedly increased melanin content and skin pigmentation of guinea pigs. Allan et al., *J. Invest. Dermatol.* 105:687–92 (1995). Dose-dependent increased pigmentation was first visible on days 17–22 and persisted for 10–14 weeks.

U.S. Pat. No. 5,514,374 to Bonte et al. uses a plant extract from black horehound for promoting skin pigmentation through melanogenesis-stimulating activity on melanocytes present in the skin or the hair follicles. U.S. Pat. No. 5,505,934 to Meybeck et al. uses an extract of topically applied *Coleus esquirolii, Coleus scutellarioides* or *Coleus xanthanthus* to promote the pigmentation of skin or hair.

U.S. Pat. No. 5,100,654 to Pawelek et al. describes the use of phosphorylated derivatives of L-dopa for increasing the content of melanin in the skin and hair. U.S. Pat. No. 4,968,497 to Wolfram et al. uses an aqueous medium containing melanin or a precursor of melanin for tanning human skin. Thorel (FR 2698785) teaches that melanogenesis may be stimulated by arachidonic acid or a derivative and a non-saponifiable vegetable fraction as a potentiator.

The presence in the skin's stratum corneum of certain metal salts can have an accelerating effect on the formation of melanin, even in the absence of exposure to sunlight. Among the metallic cations useful for this purpose are those of copper, iron, zinc and manganese. One approach to increasing pigmentation has been by coating the skin with preparations containing copper ion. The copper ion is then used to activate tyrosinase, the rate limiting enzyme in melanin biosynthesis. U.S. Pat. No. 4,349,536 to Hausler describes a oil-in-water mixture containing zinc and copper ions and anionic surfactants such as sodium lauryl sulfate for promoting suntan by topical administration to skin exposed to ultraviolet radiation. U.S. Pat. No. 5,075,102 to Hubaud et al. uses a mixture of xanthine compound and copper salt such as copper gluconate to accelerate the development of a suntan and to protecting the skin by reducing the amount of ultraviolet radiation falling on the skin.

While some copper(II) complexes can possess healing and/or anti-inflammatory properties, other copper(II) complexes can be very toxic to tissues and strongly inhibit the healing of wounds. In general, water-soluble copper(II) complexes tend to possess healing and anti-inflammatory properties while copper(II) complexes with substantial hydrophobic character tend to be toxic; however, numerous exceptions to this generalization exist.

For example, copper(II) complexes of ethylenediamine and diethylenetridiamine, which are water soluble and would be predicted to have healing activity, have been found to be toxic to cells and inhibitory to wound healing. On the other hand, the copper(II) complex of oleic acid has considerable hydrophobic character and would be predicted to be toxic, but has been reported by Heintze U.S. Pat. No. 4,123,511 to possess healing properties. Furthermore, other hydrophobic copper(II) complexes of other fatty acids such as lauric acid and caprylic acid have been reported to possess anti-inflammatory activities (Sorenson, *Inflammation* 3:317–331 (1976); *Agents and Actions* 8:305–331 (1981); and *Comprehensive Therapy* 11:49–64 (1985)).

Variation from the tendency of water-soluble copper(II) complexes to possess healing and anti-inflammatory properties may reside in the specificities of cell surface receptors which can affect or modify the general healing versus toxic generalizations described above. For example, in some cases very minor chemical differences can produce vastly different biological responses. The classic examples of this is the action of folic acid, a vitamin, compared to the very potent and toxic anti-cancer agent, methotrexate. The structures of folic acid (*Merck Index*, 11th Edition, Merck & Co., Rahway, N.J., Rahway, N.J., 1989, p.5912) and methotrexate are nearly identical. The only difference is that methotrexate contains an amine group instead of an oxygen molecule on the pteridine ring, and a methyl group at the C-9–N-10 bridge (between the pteridine and benzene rings) (Sirotnak, Burchall, Ensminger, & Montgomery, *Folate Antagonists as Therapeutic Agents*, Vol. 1, Academic Press Inc., Orlando, Fla., 1984. pp. 220–221, 290–291, 295, 308–310).

Compositions and methods are needed which accelerate natural suntanning and melanogenesis while at the same time preserving the tanned skin. While the field has developed methods to stain the skin, and in some cases improve tanning, these methods generally do not serve to protect skin health, diminish peeling, and increase the retention of tanned skin. Quite surprisingly, the present invention provides a unique skin tanning and skin repair combination that both accelerates melanogenesis and skin tanning while protecting the skin by preserving and restoring the natural integrity of the skin. When applied to damaged skin, the present invention speeds repair of the skin.

SUMMARY OF THE INVENTION

The present invention provides compositions and methods for stimulating melanogenesis in the skin of a mammal and for protecting the skin of a mammal from damage due to ultraviolet radiation. The compositions useful in these methods, including pharmaceutical compositions, are prepared from hydrolytic or enzymatic digents of protein, called peptones, complexed with an ionic metal, e.g, copper (II), indium (III), tin(II) or tin(IV), or therapeutically acceptable salts thereof. Preferably the metal is copper(II).

In one aspect methods are provided for preparing the pharmaceutical formulations useful in stimulating melanogenesis in the skin of a mammal and for protecting the skin of a mammal from damage due to ultraviolet radiation, by combining a peptone digest with an amount of an aqueous solution of ionic metal salt sufficient to induce a precipitate. Typically, the peptone digest is prepared from casein, collagen, elastin, meat products, silk protein, soybean protein, and the like, and the ionic transition metal is selected from copper(II), indium (III), tin(II) and tin(IV). The resulting complex can be combined with appropriate carriers, dispersants, etc. to produce a formulation suitable for administration to the skin as a cream, spray, lotion, gel, liquid or the like. The formulation can optionally contain other factors, including those which block UV-A and/or UV-B radiation, e.g., sunscreens or sunblocks, or healing factors, as desired.

According to the invention, the formulations are administered to the skin of a mammal in an amount sufficient to accelerate melanogenesis, typically in an amount sufficient such that the accelerated melanogenesis results in prolonged and natural-appearing increased pigmentation of the skin. Typically the skin is exposed to ultraviolet radiation after the composition is administered to the skin, although in other embodiments the skin is exposed to ultraviolet radiation before the composition is administered to the skin and the composition simultaneously reduces peeling of damaged skin. The composition can be administered on a daily basis, or more frequently, to the skin area in which enhanced melanogenesis and skin protection is desired.

DESCRIPTION OF THE SPECIFIC EMBODIMENTS

Compositions and methods are provided by the present invention for topical skin treatments to skin of mammals, especially humans, to both accelerate melanogenesis and skin tanning while protecting the skin by preserving and restoring the natural integrity of the skin. When applied to damaged skin, the present invention speeds repair.

The compositions of the invention are formed by the complexation of enzymatic protein digests (peptones) and ionic metals such as copper, iron, zinc or manganese, most preferably copper. Peptones are generally comprised of intermediate polypeptide products and mixtures of small peptides, formed in partial hydrolysis of proteins. Among the types of enzymatic protein digests useful in the invention are digests of soybean protein, casein, collagen, elastin, meat products (e.g., PRIMATONE), such as beef, liver, silk protein and so forth. By peptone digest is meant that the protein is degraded by enzymatic or hydrolytic (such as partial digestion with hydrochloric acid) digestion according to well known procedures, such as described in Remington's Pharmaceutical Sciences, Mack Publishing Co., Easton, Pa. pp. 428–429 (1975), which is incorporated herein by reference, using enzymes such as papain, etc. Many peptone digests are widely available commercially, such as from Sigma Chemical Company, St. Louis, Mo.

To produce the complexes useful in the present invention, the peptone digests are complexed with copper or the salts thereof, such as sulfate, acetate, phosphate, etc. In one method for preparing the peptone-metal complex described in copending application Ser. No. 08/369,609 and U.S. Pat. No. 5,382,431, incorporated herein by reference, a peptone is dissolved in warm water (about 40° C.) at a concentration of about 5 to 50% (weight/volume), then mixed with a aqueous solution of a copper salt (e.g., copper(II) chloride) at a salt concentration of about 10 to 50% (w/v), more preferably about 20% (w/v). The volume of metal salt solution added is that amount needed to induce a copious precipitate in the solution (about 20 to 50% of the initial volume of in the case of soybean peptone), after the pH is adjusted to between about pH 6 to pH 7 to induce maximum formation of precipitate. The precipitate contains substantial amounts of hydrophobic peptides, plus a small amount, generally about 1–10%, of the metal salt complexed to the peptides. By complexed is meant that the peptides and metal ions form electrostatic bonds, although this mechanism is offered by way of possible explanation only and not by way of limitation.

Isolation and purification of the peptone-copper complexes can then be accomplished by any suitable separation or purification procedure such as, for example, filtration, extraction, centrifugation, crystallization, or a combination of these procedures. Specific illustrations of suitable separation and isolation procedures can be had by reference to the examples hereinbelow. However, other equivalent separation or isolation procedures could, of course, also be used.

In an alternative method of preparation, the peptones and copper chloride are directly combined in warm water (about 40°–60° C.) at concentrations which are the final concentrations desired for the formulation to be applied to the host. The pH of the mixture is adjusted (with sodium hydroxide or the like) to a pH between 6.0 and 7.0, and other aqueous components, as desired, are added, followed by blending in of carriers, smootheners, etc. for preparing a final formulation. This method avoids the necessity of a centrifugation step while producing formulations at the desired copper-peptone final concentration.

The peptone-metal complexes may be administered for a variety of therapeutic, prophylactic or cosmetic uses to humans, or in veterinary applications as a skin protectant and healant to other warm-blooded animals. Among veterinary animals particularly well suited for treatment with the present compositions are species of equine, bovine, porcine, ovine, caprine, canine, etc.

The compositions and pharmaceutical preparations thereof for use as a skin protectant and tanning agent are intended for topical administration in a prophylactic and/or therapeutic or cosmetic treatment regimen. Preferably, the pharmaceutical compositions are administered locally, e.g., topically, as a paste, cream, salve, gel, droplet, spray, etc.

For administration to the skin of a human or other mammal, the peptone-metal compositions will often be sterilized or formulated to contain one or more preservatives for incorporated into pharmaceutical, cosmetic or veterinary formulations. Compositions which comprise the peptone-metal complexes can be sterilized by conventional, well known sterilization techniques, e.g., boiling or pasteurization, without substantially adversely affecting the biological activity of the peptone-copper complexes. The compositions may contain pharmaceutically acceptable auxiliary substances as required to approximate physiological conditions and as necessary to prepare compositions for convenient administration, such an pH adjusting and buffering agents, preservatives, and delivery vehicles. Actual methods for preparing pharmaceutically administrable compounds will be known or apparent to those skilled in the art and are described in detail in, for example, Remington's Pharmaceutical Science, Mack Publishing Company, Easton, Pa., 19th ed., 1995, which is incorporated herein by reference.

Depending on the intended mode of administration and the intended use, the compositions may be in the form of solid, semi-solid, or liquid dosage forms, such, for example, as powders, granules, crystals, liquids, suspensions, liposomes, pastes, creams, salves, etc., and may be in bulk or unit-dosage forms suitable for administration of relatively precise dosages. The compositions may include a conventional pharmaceutical carrier or excipient and, in addition, may include other medicinal agents, growth factors, wound sealants, carriers, etc., as further described herein. Perfumes, dyes and pigments can also be incorporated into the active compositions of the invention. These agents may simply be spread over the skin or may preferably be rubbed into the skin to enhance penetration.

For semi-solid compositions, as would be appropriate for pastes and creams intended for topical administration, the peptone-copper complexes can be provided separately or may be compounded with conventional nontoxic carriers such as, for example, aloe vera gel, squalene, glycerol stearate, polyethylene glycol, cetyl alcohol, stearic acid, and propylene glycol, among others. Such compositions may contain about 5–100% active ingredient, more preferably about 5–25%. Thus, the final concentration of copper or other metal in a formulation can range from about 0.1 or 0.15% (w/v) up to 0.4 to 0.8% or 1.6%, and in some instances up to 2 to 5% or more, although it will typically be desirable to employ the lowest final concentration of copper as possible which achieves the desired effect. The concentration of the peptone-copper complexes in these formulations can vary widely, and will be selected primarily by intended use, viscosities, etc., in accordance with the particular indication and mode of administration selected. Actual methods of preparing such dosage forms are known, or will be apparent, to those skilled in this art; for example, see Remington's Pharmaceutical Science, supra. The composition or formulation to be administered will, in any event, contain a quantity of the peptone-copper complexes sufficient to achieve the desired therapeutic or prophylactic effect in the subject being treated.

The compositions formulated for administration to the skin are administered to a warm-blooded animal, such as humans, already suffering from damaged skin (e.g., peeling) due to ultraviolet or other irradiation or oxidative skin damage in an amount sufficient to allow the healing process to proceed more quickly than if the host were not treated. Amounts adequate to accomplish these effects are defined as a "therapeutically effective doses," and will vary according to the severity of the damage, but generally will range from about 1 mg to about 50 mg per day of peptone-copper complex per day per square centimeter of treated skin, with dosages of from about 10 mg to about 25 mg per day per square centimeter of skin being more commonly used. Maintenance dosages over a prolonged period of time may be adjusted as necessary. For veterinary uses higher levels may be administered as necessary. Determining actual amounts of the peptone-copper complexes necessary to treat a particular condition as described herein will typically be through standard empirical methods well known in the art.

In prophylactic and cosmetic applications the compositions are employed for accelerating natural suntanning and melanogenesis while protecting the skin from damage. Thus, the peptone-copper complexes are administered to a host under conditions in which accelerated skin tanning or darkened pigmentation is desired so as to enhance a host's own suntanning capabilities or to provide the desired pigmentation while protecting the integrity of the skin. In these uses the precise amounts again depend on the amount of pigmentation desired and the extent and conditions under which the skin is exposed to potentially damaging conditions, such as ultraviolet radiation, but generally range from about 0.1 mg to about 10 mg per day per square centimeter of skin, more commonly from about 1 mg to about 3 mg per $cm^2$ of skin per day. Single or multiple administrations of the compositions can be carried out daily or over a prolonged period of time.

The peptone-copper complexes of the invention may be administered to the skin in relatively large amounts without serious side effects, although indiscriminate use may produce discoloration of the skin. In instances where the compositions are administered prophylactically to inhibit oxidative or biochemical damage to the skin or to those suffering from only mild skin damage, irritation or inflammation of the skin, the dose may be adjusted to lower maintenance levels.

The skin tanning and skin protective/repair-enhancing formulations of the invention, including pharmaceutical compositions, may be administered alone or as combination or adjunct therapy or prophylaxis. For example, the peptone-copper compositions can be used in combination with other skin protective factors or those found to improve other aspects of tanning or healing. In this manner a synergistic effect may be attained that yields a clinical efficacy greater than that realized with any single factor. Further, while the compositions described herein stimulate a spectrum of melanogenic and skin protective processes, skin can differ considerably in its properties and tanning patterns, leading one to utilize a combination of a composition described herein and another compound or factor. A wide variety of compositions have been reported as possessing the ability to facilitate suntanning or stimulate melanin production. In addition, the formulations can contain agents which act as sunblocks, or more specifically UV-A and/or UV-B blocking agents, such as, for example, tocopherol (U.S. Pat. No. 4,144,325 to Voyt).

Factors with reported healing properties which can be included with the metal-peptone complexes for use in the melanogenic/protective/healing formulations and methods of the present invention include, for example, epidermal growth factor, fibroblast growth factor, nerve growth factor, transforming growth factors, angiogenic growth factors, heparin, fibronectin, fibrin, platelet-derived growth factor, enzymatic superoxide dismutase, extracts of blood or factors from the blood, and other similar factors.

The following examples are offered by way of illustration, not by way of limitation.

EXAMPLE I

Preparation of Active Peptone-Metal Complexes

This Example describes methods used in the preparation of the peptone-metal complexes having biological activities described herein.

Soybean peptone is obtained from Quest International Company, Norwich, N.Y. (type HY-SOY, no. IPL;5X59022). Cupric chloride dihydrate is purchased from Ruger Chemical Company, Irvington, N.J. (no. 0824).

Soybean peptones (enzymatic digests of soybean protein) are dissolved in warm water (40° C.) at a concentration of about 20% (weight/volume), then mixed with an aqueous solution of copper chloride at a salt concentration of about 20% (w/v). The pH of each soybean peptone-copper chloride mixture is adjusted with sodium hydroxide to a pH value between 6.0 and 7.0. The resulting precipitate containing the peptone-copper complexes is removed by centrifugation at 10,000G for 20 minutes, then processed as a wet paste into further products, e.g., the sticky paste can be applied directly to the skin or more usually is formulated to a desired final concentration into creams, lotions, sprays, etc.

Alternatively, the peptones and copper chloride are combined in water (60° C.) at concentrations which are the final concentrations desired for the formulation to be applied to the host skin and the pH of the mixture adjusted (with sodium hydroxide or the like) to a pH value between 6.0 and 7.0. Other aqueous components can then be added, in addition to blending in carriers, smootheners, etc. for preparing the lotion or cream to its final formulation without the necessity of a centrifugation step.

Representative cream formulations are as follows:

I

Formulation I comprises, in approximate amounts (final concentrations, w/v %): water, 55.6; cetyl alcohol, 4.0;

ARLACEL 165 (glyceryl stearate and PEG-100 stearate), 3.0; LEXOL EHP (octyl palmitate), 4.0; copper chloride-2H$_2$0, 2.70; soybean peptone, 8.0; sodium lauryl sulfate, 12.0; mineral oil, 2.0; edetate acid, 1.0; allantoin, 0.5; citric acid, 3.0; GERMABEN-II-E (propylene glycol, diazolidinyl urea, methylparaben propylparaben), 1.0; herbal fragrance, 0.1; aloe vera powder, 2.0; vitamin A–D, 0.05; vitamin E, 0.05.

II

Formulation II comprises, in approximate amounts (final concentrations, w/v %): water, 56.3; cetyl alcohol, 4.0; ARLACEL 165, 5.0; LEXOL EHP, 4.0; squalene, 2.0; copper chloride-2H$_2$0, 2.02; soybean peptone, 8.0; sodium lauryl sulfate, 10.0; mineral oil, 2.0; edetate acid, 1.0; allantoin, 0.5; citric acid, 3.0; GERMABEN-II-E, 1.0; herbal fragrance, 0.1; aloe vera powder, 1.0; vitamin A–D, 0.05; vitamin E, 0.05.

III

Formulation III comprises, in approximate amounts (final concentrations, w/v %): water, 57.7; cetyl alcohol, 5.0; stearic acid, 2.0; ARLACEL 165, 8.0; LEXOL EHP, 4.0; squalene, 2.0; copper chloride-2H$_2$0, 1.62; soybean peptone, 6.0; sodium lauryl sulfate, 7.0; mineral oil, 2.0; edetate acid, 1.0; allantoin, 0.5; citric acid, 1.0; GERMABEN-II-E, 1.0; herbal fragrance, 0.1; aloe vera powder, 1.0; vitamin A–D, 0.03; vitamin E, 0.03.

IV

Formulation IV comprises, in approximate amounts (final concentrations, w/v %): water, 58.0; cetyl alcohol, 5.0; stearic acid, 3.0; ARLACEL 165, 7.0; LEXOL EHP, 4.0; squalene, 2.0; copper chloride-2H$_2$0, 0.81; soybean peptone, 6.0; sodium lauryl sulfate, 5.0; mineral oil, 3.0; edetate acid, 1.0; allantoin, 0.5; citric acid, 3.0; GERMABEN-II-E, 1.0; herbal fragrance, 0.1; aloe vera powder, 0.5; vitamin A–D, 0.03; vitamin E, 0.03.

V

Formulation V comprises, in approximate amounts (final concentrations, w/v %): water, 62.9; cetyl alcohol, 5.0; stearic acid, 5.0; ARLACEL 165, 7.0; LEXOL EHP, 4.0; squalene, 5.0; copper chloride-2H$_2$0, 0.40; soybean peptone, 6.0; mineral oil, 3.0; allantoin, 0.5; GERMABEN-II-E, 1.0; herbal fragrance, 0.1; aloe vera powder, 0.1; vitamin A–D, 0.01; vitamin E, 0.01.

The soybean peptone-copper complexes are used as skin tanning and protective agents that facilitate the pigmentation process (thereby accelerating tanning) while inhibiting skin damaged or irritation. The hydrophobic peptides adhere to the skin and form a protective barrier, while the complexed copper serves to impart a melanogenesis activity to the mixture.

Other types of enzymatic protein digests such as those of casein, collagen, elastin, meat products, silk protein and the like, and other salts of copper, such as sulfate, acetate, phosphate and so forth would be expected to work similarly.

EXAMPLE II

Skin research has indicated that the restoration of barrier function is a valid method for measuring the repair of damaged skin, and that skin irritations and losses such a skin peeling are primarily due to a loss of barrier function (*Skin Res. Technol.* 2:78–82 (1996), incorporated herein by reference). Transepidermal water loss (TEWL) is frequently used to quantitate the barrier restoration of damaged skin. TEWL allows for comparisons of the amount of water loss in damaged versus control skin regions. Normal skin allows for a well regulated amount of water loss, while damaged skin results in excessive water loss. Thus, barrier restoration creams can be assayed according to their ability to repair damaged skin.

An effective skin irritancy assay system has been developed which allows for the quantitative analysis of various cream products. The analysis of test creams applied to grid patterns on the backs of human volunteers (6 Total, 3 men, 3 women), using the TEWL assay, is both effective and rapid (*Skin Res. Technol.* 2:70–77 (1996), incorporated herein by reference).

Skin damage was produced by applying waterproof plastic cups, 20 mm in diameter, containing 1% of a detergent, sodium lauryl sulfate, in water, to the paravertebral skin on the backs of volunteers for 24 hours. This produced a strong irritation and damage to the skin. The test was then started and the initial rate of TEWL measured (0 hours). Two sites were used for each test on each person. Then, 50 µl of the tanning and skin repair cream V was applied to the skin. After an additional 24 hours the TEWL was again measured, and 50 µl of cream was again applied. As healing progressed, the rate of water loss decreased due to skin repair. At 48 hours after the start of the test, the final TEWL measurement was completed. The results indicated (Table 1) that the tanning and skin repair cream was effective in restoring the skin's barrier function after detergent damage.

TABLE 1

| | SLS Results | |
|---|---|---|
| | Percent recovery (Full Recovery = 100%) | |
| | 24 hours | 48 hours |
| Control - Untreated | –13.0 | –4.55 |
| Healing cream | 14.6 | 30.5 |
| p value difference | P = <0.05 | P = <0.05 |

EXAMPLE III

The methods in this Example were identical to those in Example II except that the skin damaging agent was a lipid solvent, acetone, which was applied to the skin of volunteers (6 total, 3 men, 3 women) for 24 hours. Two sites were used for each test on each person. This solvent produced a raw reddish skin somewhat like a burn. Immediately afterward, the healing cream was applied (50 µl) to the resultant irritated skin. The cream was reapplied at 24 and 48 hours later. TEWL was measured at 0 hours, 24 hours, and 48 hours. The results indicated (Table 2) that the tanning and skin repair cream was effective in restoring the skin's barrier function after acetone damage.

TABLE 2

| | Acetone Results | |
|---|---|---|
| | Percent recovery (Full Recovery = 100%) | |
| | 24 hours | 48 hours |
| Control - Untreated | 17.0 | 44.8 |
| Healing cream | 46.8 | 69.6 |
| p value difference | P = <0.01 | P = <0.01 |

EXAMPLE IV

As in Example III, the peptone-copper cream was applied to the skin of six human volunteers as above but to undamaged skin. After 5 days, it was found that skin pigmentation had markedly increased in the area to which the cream had been applied. The pigmentation could not be rubbed off or scrapped from the skin. The pigmentation had the color of natural melanin.

These results indicated that the peptone-copper cream could induce melanogenesis in the absence of sunlight or ultraviolet radiation.

EXAMPLE V

In persons with sunburn, peptone-copper cream stopped the loss of burned skin (diminished peeling) and increased the tanning of skin. The darkening of the skin was due to increased melanin in the skin and persisted for several months.

EXAMPLE VI

A 32 year old man had a very lightly pigmented skin and was prone to sunburn. Attempts to tan his skin invariably produced sunburn and peeling. By using peptone-copper tanning and skin repair cream, he developed a rich full tan after brief suntanning and experienced no subsequent skin peeling.

EXAMPLE VII

A 35 year old man with a lightly pigmented skin and a tendency of peel applied a daily light coating of the peptone-copper tanning and skin repair cream to his body while at a tropical beach resort. He developed a deep tan and had no subsequent peeling.

EXAMPLE VIII

A 47 year old man had a very lightly pigmented skin and a tendency of easily sunburn. Every day for 5 days, he applied a light coating of peptone-copper cream to his face before skiing for the day. After one week he developed a deep tan and had no subsequent peeling of the skin.

EXAMPLE IX

A 48 year old woman with a very light complexion and a tendency to sunburn and peel used peptone-copper cream for one week while gardening. She developed a deep brownish-red tan and had no subsequent peeling.

It is evident from the above results that the subject invention provides formulations of peptone-metal complexes for topical skin administration to accelerate skin tanning and melanogenesis while simultaneously providing a protective function for the treated skin. The peptone-metal formulations are also effective to enhance the recovery of skin which has been damaged by ultraviolet radiation, excessive oxidation, or the like, and enhances the tissue regenerative processes in the epidermis. The invention also provides economical methods for preparing and formulating the compositions for topical administration.

All publications and patents mentioned in this specification are indicative of the level of skill of those skilled in the art to which this invention pertains. All publications and patents are herein incorporated by reference to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for stimulating melanogenesis in the skin of a mammal which comprises:

administering to the skin a composition which comprises a peptone digest complexed with an ionic metal in an amount sufficient to accelerate melanogenesis.

2. The method of claim 1, wherein the ionic metal is copper(II), indium (III), tin(II) or tin(IV), and therapeutically acceptable salts thereof.

3. The method of claim 1, wherein the ionic metal is copper(II).

4. The method of claim 1, wherein the peptone digest is prepared from casein, collagen, elastin, meat products, silk protein, or soybean protein.

5. The method of claim 1, wherein the peptone digest is prepared from soybean protein.

6. The method of claim 5, wherein the ionic metal complexed with the soybean peptone is copper(II).

7. The method of claim 1, wherein the melanogenesis which is stimulated results in an increased pigmentation of the skin.

8. The method of claim 1, wherein the skin is exposed to ultraviolet radiation after the composition is administered to the skin.

9. The method of claim 1, wherein the skin is exposed to ultraviolet radiation before the composition is administered to the skin and the composition simultaneously reduces peeling of damaged skin.

10. The method of claim 1, wherein the composition is administered to the skin as a cream, spray, lotion, gel or liquid.

11. The method of claim 1, wherein the composition is administered on a daily basis to the skin area in which enhanced melanogenesis is desired.

* * * * *